(12) United States Patent
Havel (10) Patent No.: US 7,181,275 B2
(45) Date of Patent: Feb. 20, 2007

(54) METHOD AND APPARATUS FOR ACTIVELY DETERMINING A COUPLING INTERVAL CORRESPONDING TO A CARDIAC VULNERABLE ZONE

(75) Inventor: William J. Havel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 182 days.

(21) Appl. No.: 10/745,035

(22) Filed: Dec. 23, 2003

(65) Prior Publication Data

US 2005/0137639 A1  Jun. 23, 2005

(51) Int. Cl.
*A61N 1/39* (2006.01)
(52) U.S. Cl. ............................................. 607/7; 607/28
(58) Field of Classification Search ................... 607/27, 607/28, 5–8
See application file for complete search history.

(56) References Cited

U.S. PATENT DOCUMENTS

| | | | |
|---|---|---|---|
| 4,280,502 A | 7/1981 | Baker et al. | |
| 4,374,382 A | 2/1983 | Markowitz et al. | |
| 5,086,774 A * | 2/1992 | Duncan | 607/9 |
| 5,105,809 A | 4/1992 | Bach et al. | |
| 5,107,833 A | 4/1992 | Barsness | |
| 5,117,824 A | 6/1992 | Keimel et al. | |
| 5,129,392 A | 7/1992 | Bardey et al. | |
| 5,143,081 A * | 9/1992 | Young et al. | 600/554 |
| 5,168,871 A | 12/1992 | Grevious | |
| 5,279,293 A | 1/1994 | Andersen et al. | |
| 5,292,343 A | 3/1994 | Blanchette et al. | |
| 5,314,450 A | 5/1994 | Thompson | |
| 5,324,315 A | 6/1994 | Grevious | |
| 5,346,506 A | 9/1994 | Mower et al. | |
| 5,354,319 A | 10/1994 | Wyborny et al. | |
| 5,383,909 A | 1/1995 | Keimel | |
| 5,395,373 A * | 3/1995 | Ayers | 607/8 |
| 5,458,623 A * | 10/1995 | Lu et al. | 607/28 |
| 5,545,186 A | 8/1996 | Olson et al. | |
| 5,564,422 A | 10/1996 | Chen et al. | |
| 5,609,618 A | 3/1997 | Archer | |
| 5,643,323 A | 7/1997 | Kroll et al. | |

(Continued)

OTHER PUBLICATIONS

Scwhartz, "Influence of T-Wave Shock Energy on Ventricular Fibrillation Vulnerability in Humans", *Journal of American College of Cardiology 1995 Conference Abstracts*, Feb. 1995.

(Continued)

*Primary Examiner*—Scott M. Getzow
(74) *Attorney, Agent, or Firm*—Michael C. Soldner; Girma Wolde-Michael (57) ABSTRACT

A method and apparatus for actively determining a coupling interval corresponding to a cardiac vulnerable zone associated with a therapy of an implantable medical device that includes a timing and control unit delivering, via electrodes of a plurality of electrodes, a first pulse train and a first pulse signal at a predetermined time interval from delivery of a last pulse of the first pulse train. A sensor determines an evoked response corresponding to the first pulse signal, and a microprocessor compares the evoked response to a prior determined evoked response and sets the coupling interval equal to the predetermined time interval in response to the evoked response having increased by a first predetermined amount, and reduces the predetermined time interval by a second predetermined amount in response to the evoked response not having increased by the first predetermined amount.

20 Claims, 9 Drawing Sheets

U.S. PATENT DOCUMENTS

| | | |
|---|---|---|
| 5,649,971 A | 7/1997 | Fain et al. |
| 5,653,740 A | 8/1997 | Degroot et al. |
| 5,755,736 A | 5/1998 | Gillberg et al. |
| 5,954,753 A * | 9/1999 | Alt et al. ............. 607/8 |
| 5,987,356 A | 11/1999 | DeGroot |
| 6,052,621 A * | 4/2000 | Begemann et al. ......... 607/28 |
| 6,154,672 A * | 11/2000 | Pendekanti et al. ......... 607/5 |
| 6,246,908 B1 | 6/2001 | Chattipakorn et al. |
| 6,477,422 B1 | 11/2002 | Splett |
| 6,738,669 B1 * | 5/2004 | Sloman et al. .......... 607/28 |
| 6,834,204 B2 * | 12/2004 | Ostroff et al. .......... 607/2 |
| 2004/0106955 A1 * | 6/2004 | Swerdlow et al. ........ 607/7 |

OTHER PUBLICATIONS

Watanabe, "The Management of Paroxysmal Supraventricular Tachycardia Using a Scanning Pacemaker System", *Cardiac Pacing*, 1997, pp. 187-190.

\* cited by examiner

METHOD AND APPARATUS FOR ACTIVELY DETERMINING A COUPLING INTERVAL CORRESPONDING TO A CARDIAC VULNERABLE ZONE

FIELD OF THE INVENTION

The present invention relates generally to implantable medical devices, and in particular, the present invention relates to a method and apparatus for actively determining a coupling interval corresponding to a cardiac vulnerable zone associated with a therapy of an implantable medical device.

BACKGROUND OF THE INVENTION

It has long been recognized that cardiac defibrillation—the termination of an episode of fibrillation—can be accomplished through application of an electrical shock to the cardiac muscle and that fibrillation can be induced by stimulating the ventricles during the vulnerable zone. See, for example, Swartz et al., "Influence of T-Wave Shock Energy on Ventricular Fibrillation Vulnerability in Humans," Journal of American College of Cardiology, 1995 Conference Abstracts, February 1995; see also, Karolyi et al., "Timing of the T-Wave Shock for Inducing Ventricular Fibrillation in Patients With Implantable Cardioverter Defibrillators," PACE NASPE Abstracts, Vol. 18, April 1995 (Part II), p. 802. Numerous types of defibrillating devices, both external and implantable, are available for the purpose of cardiac defibrillation through electrical stimulation.

When implanting an implantable medical devices for defibrillating a patient's heart, such as an implantable defibrillator device or an implantable pacemaker/cardioverter/defibrillator device, for example, it is desirable to test the device's operability to ensure that it is capable of reliably defibrillating the heart. One method of testing a defibrillator's operability to ensure that it is capable of reliably defibrillating the heart involves first inducing an episode of fibrillation in the patient's heart, and then activating the defibrillator to ascertain whether it is capable of terminating the induced fibrillation. Current implantable defibrillators operate to induce fibrillation in either chamber of the heart (atrial or ventricular) by delivering a stimulus during that chamber's repolarization phase, i.e., within a so-called "vulnerability window" following the chamber's depolarization period when the heart has begun to repolarize but has not completely repolarized. This is described, for example, in U.S. Pat. No. 5,129,392 to Bardy et al., entitled "Apparatus for Automatically Inducing Fibrillation," which patent is assigned to assignee of the present invention and hereby incorporated by reference herein in its entirety.

In order to maximize efficiency of the implantable medical device, it is necessary to determine as accurately as possible the minimal energy level necessary to defibrillate the patient's heart, i.e., the defibrillation threshold (DFT) after the device and leads are implanted. The upper limit of vulnerability (ULV) has been used as an alternate to defibrillation threshold testing. The upper limit of vulnerability is defined as the minimum strength of a shock delivered into the vulnerable zone of the cardiac cycle that will not result in the induction of ventricular fibrillation. Timing the shock so that it occurs in the vulnerable zone is critical since any shock strength delivered outside the vulnerable zone will not fibrillate, resulting in an underestimate of the defibrillation threshold. As a result, one of the difficulties involved in employing an electrical shock to the cardiac muscle to induce fibrillation is determining the timing interval best suited for delivering the shock. Current methods for determining the timing or coupling interval of the shock involve identifying a point on the patient's T-wave and delivering shocks with respect to that point. Often, several coupling intervals are scanned in the vicinity of the T-wave to be sure the vulnerability zone has not been missed. Extra shocks mean extra time and possible extra discomfort to the patient during implant testing of the implantable medical device.

BRIEF DESCRIPTION OF THE DRAWINGS

Various aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Figure 1:
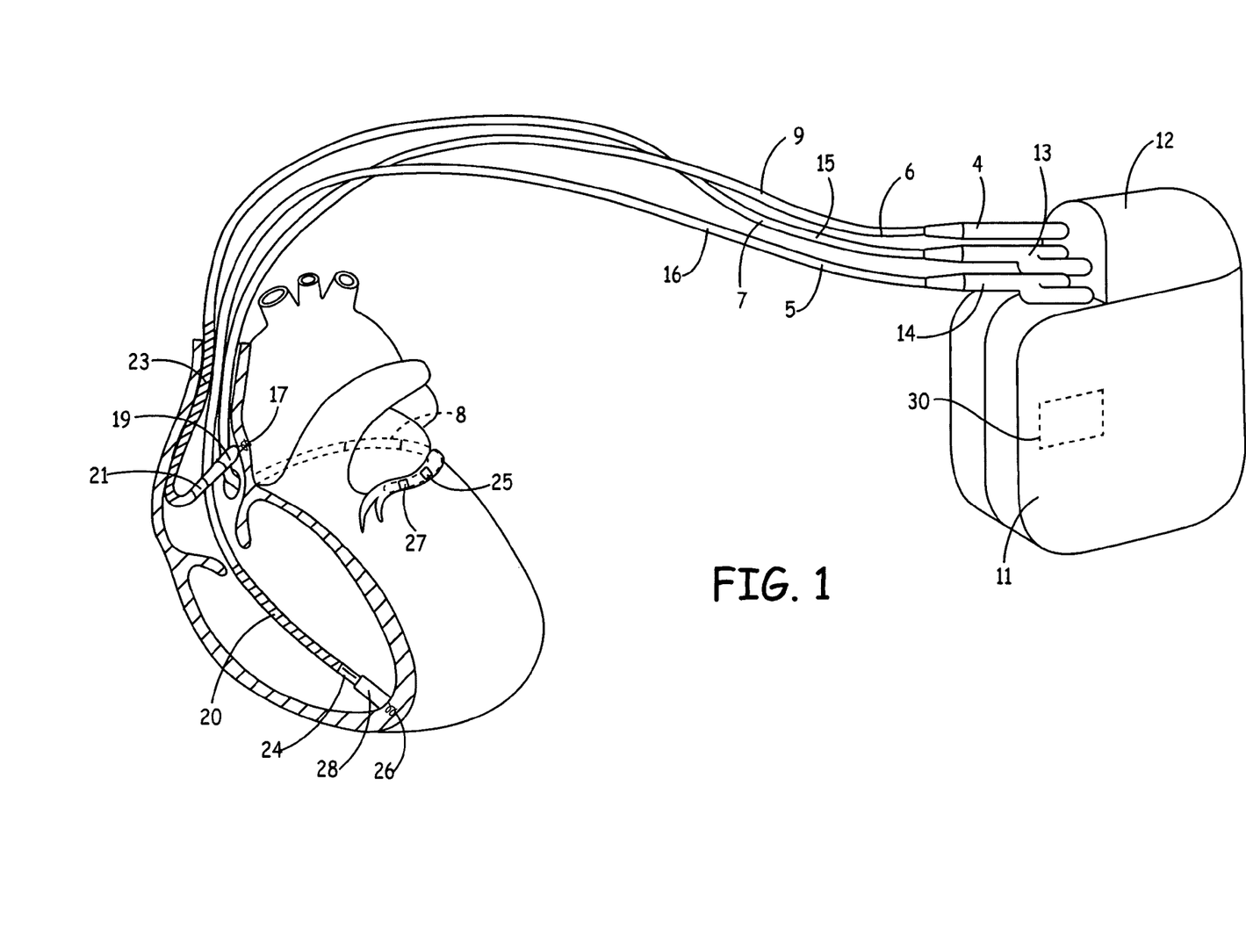
FIG. 1 is a schematic diagram of an exemplary implantable medical device in which the present invention may usefully be practiced.

FIG. 1 is a schematic diagram of an exemplary implantable medical device in which the present invention may usefully be practiced. As illustrated in FIG. 1, an implantable medical device 10 according to the present invention includes a ventricular lead 5 having an elongated insulative lead body 16 carrying three mutually insulated conductors. Located adjacent the distal end of the lead 5 are a ring electrode 24, an extendable helix electrode 26, mounted retractably within an insulative electrode head 28, and an elongated coil electrode 20. Each of the electrodes 20, 24 and 26 is coupled to one of the three conductors within the lead body 16. Electrodes 24 and 26 are employed for cardiac pacing and for sensing ventricular depolarizations, and electrode 20 is employed for cardioversion and/or defibrillation and for sensing depolarizations, as described below. At the proximal end of the lead 5 is a bifurcated connector 14, which carries three electrical connectors, each coupled to one of the coiled conductors.

An atrial/SVC lead 7 includes an elongated insulative lead body 15, also carrying three mutually insulated conductors. Located adjacent the J-shaped distal end of the lead 7 are a ring electrode 21 and an extendible helix electrode 17, mounted retractably within an insulative electrode head 19. Each of the electrodes 17 and 21 is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead 7 is a bifurcated connector 13, which carries three electrical connectors, each coupled to one of the coiled conductors.

A coronary sinus/coronary vein lead 9 includes an elongated insulative lead body 6, carrying three conductors, one of which is coupled to an elongated coiled defibrillation electrode 8. Electrode 8, illustrated in broken outline, is located within the coronary sinus and great vein of the heart. Located adjacent the distal end of lead 9 are a ring electrode 25 and a tip electrode 27. Each of electrodes 25–27 is coupled to one of the remaining two of the three conductors located within lead body 6. At the proximal end of the lead 9 is a connector plug 4 that carries an electrical connector, coupled to the coiled conductors.

The implantable medical device 10 includes a hermetically sealed enclosure 11 containing the electronic circuitry (FIG. 2) used for generating cardiac pacing pulses for delivering cardioversion and defibrillation shocks and for monitoring the patient's heart rhythm. Implantable medical device 10 is shown with the lead connector assemblies 4, 13 and 14 inserted into the connector block 12, which serves as a receptacle and electrical connector for receiving the connectors 4, 13 and 14 and interconnecting the leads to the circuitry within enclosure 11.

Insulation of the outward facing portion of the housing 11 of the implantable medical device 10 may be provided or a portion 30 of the outward facing portion may instead be left uninsulated, or some other division between insulated and uninsulated portions may be employed. The uninsulated portion 30 of the housing 11 optionally serves as a subcutaneous defibrillation electrode, used to defibrillate either the atria or ventricles, and as a sensing electrode for sensing depolarizations of the heart. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 2:
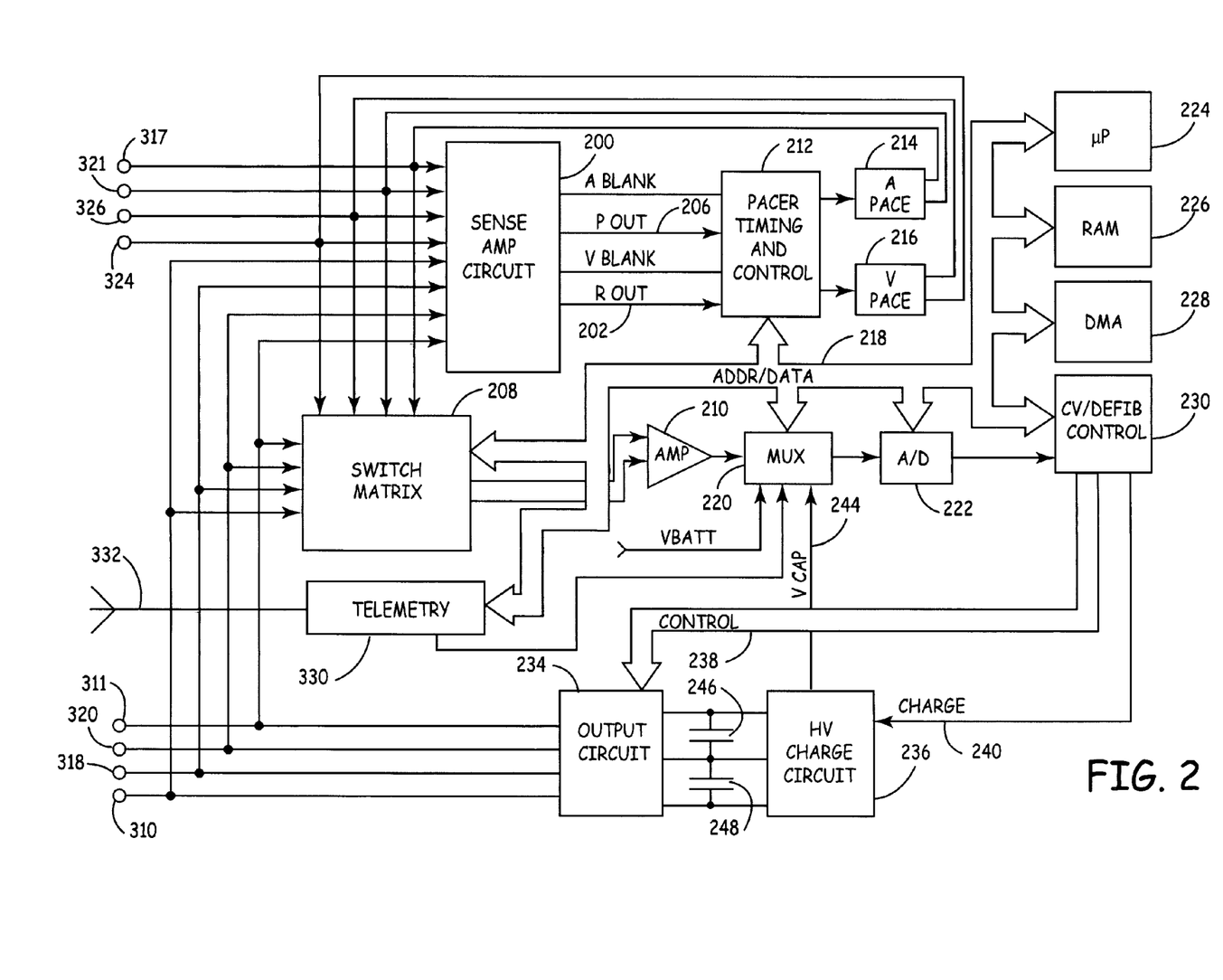
FIG. 2 is a functional block diagram of an exemplary implantable medical device of the type illustrated in FIG. 1, in which the present invention may usefully be practiced.

FIG. 2 is a functional block diagram of an exemplary implantable medical device of the type illustrated in FIG. 1, in which the present invention may usefully be practiced. The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to an electrode formed along the uninsulated portion 30 of the housing of the implantable medical device 10. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 23 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 310, 311, 318 and 320 are coupled to high voltage output circuit 234. Electrodes 324 and 326 are coupled to an R-wave amplifier, which preferably takes the form of an automatic gain controlled amplifier providing an adjustable sensing threshold as a function of the measured R-wave amplitude, included in a sense amplifier circuit 200. A signal is generated on R-out line 202 whenever the signal sensed between electrodes 324 and 326 exceeds the present sensing threshold.

Electrodes 317 and 321 are coupled to a P-wave amplifier, which preferably also takes the form of an automatic gain controlled amplifier providing an adjustable sensing threshold as a function of the measured R-wave amplitude, included in sense amplifier circuit 200. A signal is generated on P-out line 206 whenever the signal sensed between electrodes 317 and 321 exceeds the present sensing threshold. The general operation of the R-wave and P-wave amplifiers of sense amplifier circuit 200 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal processing. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits of sense amplifier circuit 200 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, PR intervals and R-P intervals, which measurements are stored in memory 226 and are used in conjunction with the present invention to measure heart rate variability and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

Arrhythmia detection may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Giliberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 3:
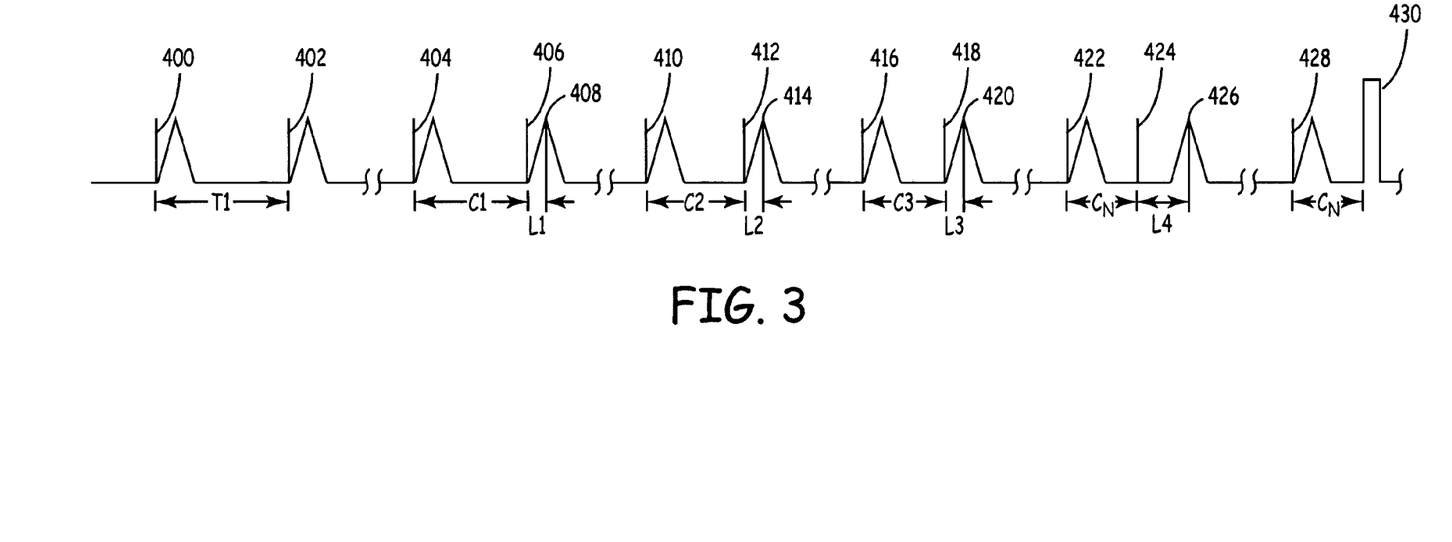
FIG. 3 is a simulated EKG strip illustrating application of a method and apparatus for actively determining a coupling interval according to the present invention.

FIG. 3 is a simulated EKG strip illustrating application of a method and apparatus for actively determining a coupling interval according to the present invention. The coupling interval determining function could be associated with determining a coupling interval associated with the most vulnerable point in the cardiac cycle, such as a T-shock coupling interval or an upper limit of vulnerability shock interval, for example. The function may be initiated by the device once the device is implanted, or may be initiated by the physician by means of a programmer or other device located external to the patient that provides signals to the implantable medical device 10 via telemetry circuitry 330.

According to an embodiment of the present invention, once the coupling interval determining function is initiated, implantable medical device 10 begins pacing the heart at a rate in excess of the patient's resting heart rate, so that it may overdrive the patient's heart. Implantable medical device 10 performs such overdrive pacing, for example, by delivering pacing pulses between ring electrode 24 and tip electrode 26 (FIG. 1), with the rate at which the pulses are delivered being programmably selected by the physician. For example, as illustrated in FIG. 3, according to an embodiment of the present invention, the pacing pulses are delivered between electrodes 24 and 26 at a rate of 150 beats per minute (bpm) so that an interval T1 separating pacing pulses 400 and 402 is approximately 400 ms. Overdrive pacing continues at this rate via electrodes 24 and 26 for a predetermined number of pacing pulses, such as eight pacing pulses, for example, separated by T1 intervals. This sequence of pacing pulses is commonly referred to as a "drive train". Only the first interval T1 is illustrated in FIG. 3 in order to simplify the description.

Once the final such pacing pulse 404 of the predetermined number of pacing pulses is delivered, a subsequent extra-stimulus pacing pulse 406 is generated at a predetermined initial interval C1 corresponding to the period of time between delivery of final pacing pulse 404 and the subsequent delivery of pacing pulse 406. The length of interval C1 is programmable, so that the physician is able to program interval C1 to be set at any desired length. For example, according to an embodiment of the present invention, interval C1 is set to be approximately equal to 280 ms. In addition, the amplitude and pulse width of the predetermined number of pacing pulses 400–404, and the amplitude and pulse width of pacing pulse 406 are programmable and may be set at any desired values. For example, according to an embodiment of the present invention, both the predetermined number of pacing pulses 400–404 and pacing pulse 406 have a programmed amplitude and pulse width of 5 volts and 1 ms, respectfully.

Following delivery of pacing pulse 406, implantable medical device 100 determines the latency of the evoked response resulting from pacing pulse 406 utilizing a combination of electrodes 8, 17, 20, 21, 23, 24, 26 and 30 to determine a far field sensing signal corresponding to the evoked response. For example, according to an embodiment of the present invention, once pacing pulse 406 is delivered, the resulting evoked response 408 is sensed using defibrillation electrode 20 and uninsulated portion 30 of housing 11 of implantable medical device 10. Once evoked response 408 is sensed via electrodes 20 and 30, microprocessor 224 determines the latency of the evoked response, i.e., the time period $L_1$ between the delivery of pacing pulse 406 and the sensing of the evoked response 408, and stores the latency of the evoked response 408 resulting from pacing pulse 406 in memory 226.

It is understood that although sensing of the evoked response is described above as being performed between electrodes 20 and 30, according to the present invention, far field sensing of the evoked response may also be performed using other electrode configurations. For example, the evoked response may be sensed between electrode 30 and one of electrodes 8, 23, 25 and 27.

Implantable medical device 10 again paces the heart at the overdrive pacing rate, triggering generation of the predetermined number of pacing pulses (i.e., eight pacing pulses) separated by interval T1. Once a final pacing pulse 410 of the predetermined number of delivered pacing pulses is delivered, a subsequent extra-stimulus pacing pulse 412 is generated at a predetermined time interval C2 from the delivery of final pacing pulse 410. According to the present invention, interval C2 is less than interval C1 by a predetermined fixed amount, such as 20 ms, for example, or is reduced from interval C1 by a predetermined percentage, such as 15%, for example. Once pacing pulse 412 is delivered, the resulting evoked response 414 is sensed using defibrillation electrode 20 and uninsulated portion 30 of housing 11 of implantable medical device 10, for example. Microprocessor 224 then determines the latency of evoked response 414, i.e., the time period $L_2$ between the delivery of pacing pulse 412 and the sensing of evoked response 414, and stores the latency of evoked response 414 in memory 226. Microprocessor 224 then compares the latency of evoked response 414 with the latency of evoked response 408, and determines whether evoked response 414 has increased from the previous measured latency of evoked response 408 by a predetermined percentage.

Implantable medical device 10 again paces the heart at the overdrive pacing rate, triggering generation of the predetermined number of pacing pulses (i.e., eight pacing pulses) separated by interval T1. Once the final such pacing pulse 416 is delivered, a subsequent extra-stimulus pacing pulse 418 is generated at a predetermined time interval C3 from the delivery of final pacing pulse 416. Interval C3 is less than interval C2 by the predetermined fixed amount or is reduced from inter C2 by the predetermined percentage. Once pacing pulse 418 is delivered, the resulting evoked response 420 is sensed using defibrillation electrode 20 and uninsulated portion 30 of housing 11 of implantable medical device 10, for example. Microprocessor 224 then determines the latency of evoked response 420, i.e., the time period $L_3$ between the delivery of pacing pulse 418 and the sensing of evoked response 420, and stores the latency of evoked response 418 in memory 226. Microprocessor 224 then compares the latency of evoked response 418 with the initially determined latency of evoked response 408, and determines whether evoked response 418 has increased from the previously measured latency of evoked response 408 by the predetermined percentage.

The process continues in this manner, reducing time interval $C_N$ corresponding to the delivery of the extra-stimulus pulse following delivery of the last pacing pulse of the predetermined number of pacing pulses until a resulting latency of the evoked response $L_N$ corresponding to interval $C_N$ is determined to have increased from the previously measured latency of evoked response by the predetermined percentage. For example, as illustrated in FIG. 3, once the final pacing pulse 422 of the generated predetermined number of pacing pulses separated by interval T1 is delivered, and a subsequent pacing pulse 424 is generated at a predetermined initial time interval $C_N$ from the delivery of final pacing pulse 422, with interval $C_N$ being either less than interval $C_{N-1}$ by the predetermined fixed amount or reduced from interval $C_{N-1}$ by the predetermined percentage, the resulting evoked response 426 is sensed using defibrillation electrode 20 and uninsulated portion 30 of housing 11 of implantable medical device 10, or other combination of electrodes 8, 17, 20, 21, 23, 24, 26 and 30 as described above. Microprocessor 224 then determines the latency of evoked response 426, i.e., the time period $L_N$ between the delivery of pacing pulse 424 and the sensing of evoked response 426, and stores the latency of evoked response 426 in memory 226. Microprocessor 224 then compares the latency of evoked response 426 with the latency of evoked response 408 and determines whether the latency of evoked response 426 has increased from the measured latency of evoked response 408 by the predetermined percentage.

If the latency of evoked response 426 is determined to have increased by the appropriate predetermined amount, interval $C_N$ is determined to be the desired coupling interval for placing a coupling shock or extra-stimulus pulse, such as a T-shock for inducing fibrillation, or a ULV shock, after the subsequent delivery of the final pacing pulse of the predetermined number of delivered pacing pulses separated by interval T1. Therefore, once the final pacing pulse 428 of the subsequently generated predetermined number of pacing pulses separated by interval T1 is delivered, a T-shock 430 or coupling shock is generated at the predetermined time interval $C_N$ from the delivery of final pacing pulse 428.

Figure 4:
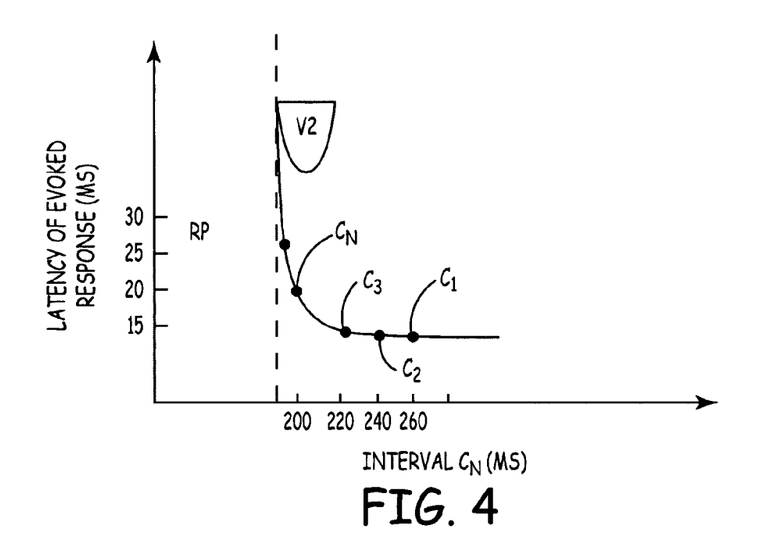
FIG. 4 is a graphical representation of the application of a method and apparatus for actively determining a coupling interval according to the present invention.

FIG. 4 is a graphical representation of an exemplary application of a method and apparatus for actively determining a coupling interval according to the present invention. As illustrated in FIG. 4, the measured latency of the evoked response taken at intervals outside of time intervals associated with the vulnerability zone VZ and the refractory period RF remains relatively flat over a range of time intervals, as illustrated by intervals $C_1$, $C_2$, $C_3$, and $C_N$. However, as the interval $C_N$ is reduced and approaches the refractory period RF, there tends to be a dispersion in conduction leading to increased latencies, which is due to dispersion of refractoriness, indicated by the increase in the latency of the evoked response, illustrated in FIG. 4 by the upward trend in the latency of evoked response as the interval $C_N$ is reduced. Such dispersion in refractoriness marks a likely location of the vulnerability zone VZ. Therefore, according to the present invention, once the measured latency of the evoked response is determined to have increased by a predetermined amount from measured latencies along the relatively flat range of time intervals, such as a 20% increase, for example, suggesting a dispersion of conduction and dispersion of refractoriness from the previous cycle, the interval $C_N$ associated with that increased latency of the evoked response is then utilized for delivery of the T-shock in the next cycle. As a result, once the final pacing pulse of the subsequently generated predetermined number of pacing pulses separated by interval T1 is delivered, a T-shock is generated at the predetermined time interval $C_N$ from the delivery of final pacing pulse.

In particular, for example, as illustrated in FIGS. 3 and 4, the latency of the evoked response corresponding to interval $C_1$ is determined to be 15 ms and the measured latency of the evoked response 426 for interval $C_N$ is 20 ms. Therefore, the latency of evoked response 426 for interval $C_N$ is determined to have increased from the measured latency of evoked response 408 by the predetermined percentage, i.e., a 20% increase in 15 ms is 18 ms, and 20 ms is greater than 18 ms. As a result, interval $C_N$ is determined to be the desired interval for placing a T-shock for inducing fibrillation after the subsequent delivery of the final pacing pulse of the predetermined number of delivered pacing pulses separated by interval T1. Therefore, once the final pacing pulse 428 of the subsequently generated predetermined number of pacing pulses separated by interval T1 is delivered, T-shock 430 is generated, spaced from the final pacing pulse 428 using time interval $C_N$ equal to 200 ms.

It is understood that the predetermined amount of increase in the latency of the evoked response that is used to trigger a determination indicating a dispersion of conduction and dispersion of refractoriness from the previous cycle is programmable, and can therefore be set at any percentage of the initially determined latency or predetermined value, and is not intended to be limited to the use of 20%, describe in the example above.

Figure 5:
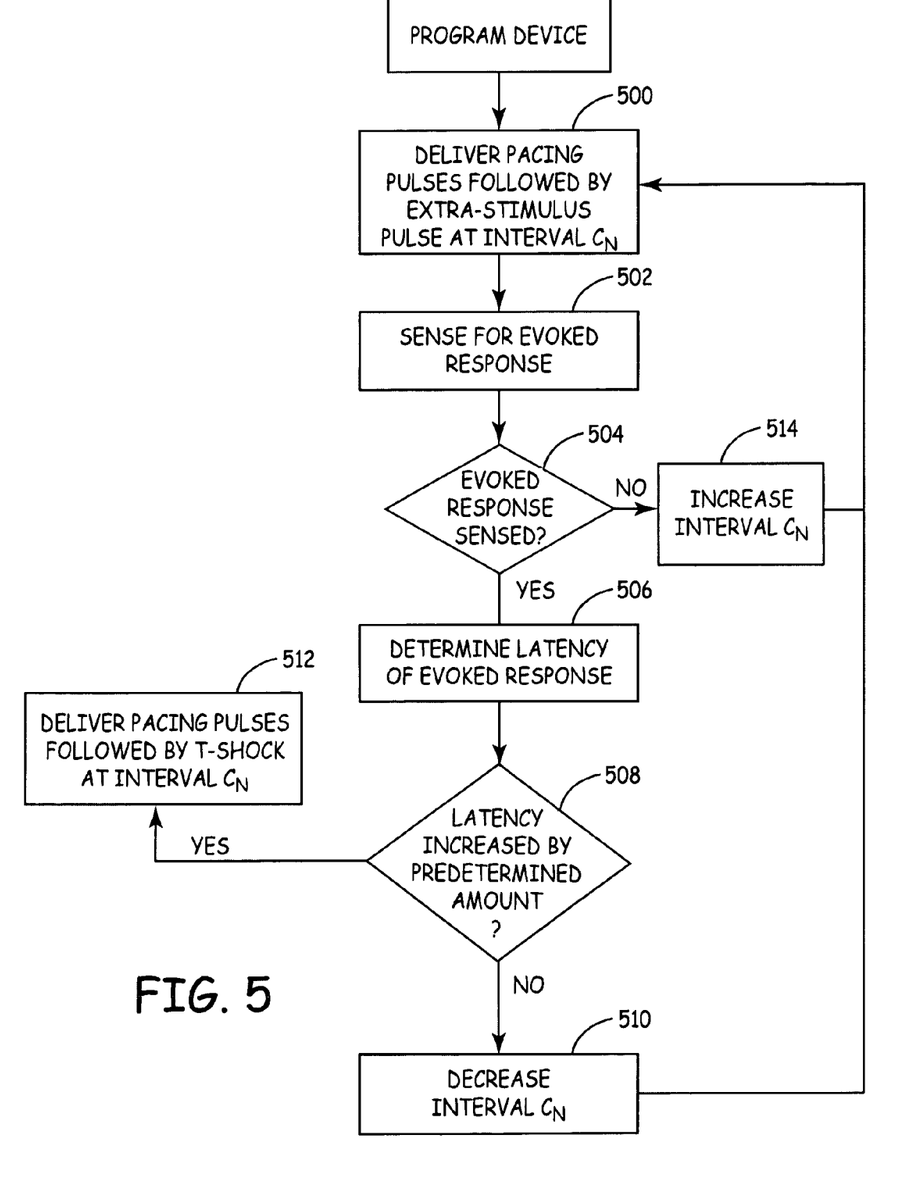
FIG. 5 is a flowchart of a method for actively determining a coupling interval according to an embodiment of the present invention.

FIG. 5 is a flowchart of a method for actively determining a coupling interval according to the present invention. As illustrated in FIGS. 4 and 5, a method for actively determining a coupling interval according to the present invention includes delivering a predetermined number of pacing pulses separated by interval T1 followed by an extra-stimulus pulse delivered at a predetermined initial time interval $C_N$ from the delivery of a final pacing pulse of the delivered pacing pulses, Step 500. Once the final pacing pulse is delivered, sensing of the evoked response resulting from delivery of the extra-stimulus pulse is initiated via a far-field sensing vector formed between two of electrodes 8, 17, 20, 21, 23, 24, 26 and 30, Step 502. A determination is then made as to whether an evoked response was sensed via the far-field sensing vector within a predetermined window of time, Step 504. If it is determined that the evoked response was sensed within a predetermined window of time, YES in Step 504, the resulting latency of the evoked response interval corresponding to the time period between the delivery of the extra-stimulus pulse and the sensed evoked response is determined and stored, Step 506. The resulting latency of the evoked response is compared to the resulting latency of the evoked response corresponding to a previous cycle to determine whether the latency of the evoked response has increased by a predetermined amount, Step 508.

If it is determined that the latency of the evoked response has not increased by the predetermined amount, NO in Step 508, the time interval $C_N$ is decreased by the predetermined amount, i.e., 20 ms, for example, Step 510, and the process is repeated using the decreased time interval $C_N$. On the other hand, if it is determined that the latency of the evoked response has increased by the predetermined amount, YES in Step 508, subsequent delivery of the predetermined number of pacing pulses separated by interval T1 is followed by delivery of a T-shock at the time interval $C_N$ associated with the increased latency of the evoked response, Step 512.

Figure 4A:
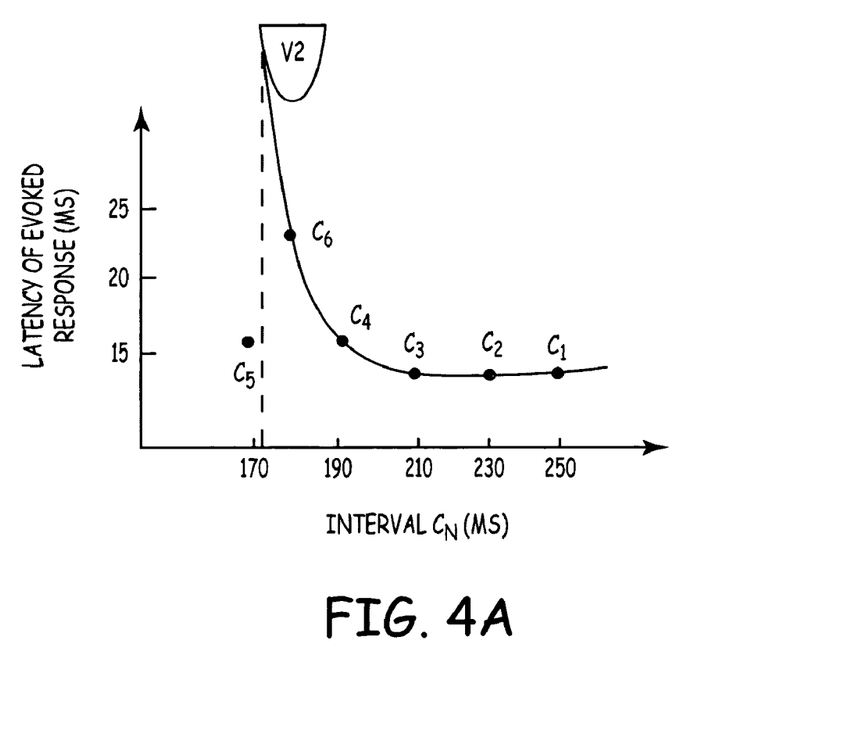
FIG. 4A is a graphical representation of the application of a method and apparatus for actively determining a coupling interval according to the present invention.

If the evoked response was not sensed within the predetermined window of time the selected time interval $C_N$ is likely too short, resulting in the final pacing pulse being delivered within the refractory period RP. Therefore, if it is determined that the evoked response was not sensed within the predetermined window of time, NO in Step 504, the subsequent time interval $C_N$ is increased by a predetermined period of time in order to re-map the latency outside of the refractory period RP, Step 514. For example, as illustrated in FIG. 4A, if time interval $C_5$ for delivery of the extra-stimulus pacing pulse falls within the refractory period and therefore an associated evoked response is not sensed within the predetermined window of time, NO in Step 504, the next time interval $C_6$ is increased by being set as a value between time interval $C_5$ and time interval $C_4$. For example, according to an embodiment of the present invention, the next time interval $C_6$ is set as being approximately equal to the time interval located at the midpoint between the time interval $C_5$ and time interval $C_4$, i.e., interval $C_6$=(time interval $C_4$+time interval $C_5$)/2. However, according to another embodiment of the present invention, the next time interval $C_6$ is increased by reducing the predetermined time interval between the final pacing pulse and the extra stimulus pacing pulse.

For example, as illustrated in FIG. 4A, assuming that interval $C_N$ is initially set to be reduced by a predetermined time interval of 20 ms for each pacing sequence, if interval $C_1$ is set as 250 ms, each subsequent interval is reduced by 20 ms. As a result, interval $C_2$ is set as interval $C_1$–20 ms, or 230 ms, interval $C_3$ is set as interval $C_2$–20 ms, or 210 ms, interval $C_4$ is set as interval $C_3$–20 ms, or 190 ms, and interval $C_5$ is set as interval $C_4$–20 ms, or 170 ms. Since $C_5$ is located within the refractory period RP, the corresponding evoked response will not be sensed within the predetermined window of time in Step 504. As a result, the subsequent interval $C_6$ is increased, Step 514, by reducing the predetermined time interval for reducing interval $C_N$.

In particular, subsequent to determining that an evoked response was not sensed for interval $C_5$, the present invention reduces the predetermined time interval from 20 ms to a shorter interval, such as 10 ms, for example, and the next interval $C_6$ is set using the reduced predetermined time interval. Thus, as illustrated in FIG. 4A, interval $C_6$ is set as interval $C_5$–10 ms, or 180 ms.

The process then continues using the new predetermined time interval for reducing the coupling interval $C_N$ so that implantable medical device 10 again paces at the overdrive pacing rate for the predetermined number of pacing pulses separated by interval T1 followed by the extra-stimulus pulse delivered at the increased interval $C_6$, Step 500 and the process is repeated as described above until the latency of the evoked response is determined to have increased by the predetermined amount, YES in Step 508.

In the example illustrated in FIG. 4A, since the latency of the evoked response corresponding to interval $C_6$ is determined to be approximately 23 ms, which is greater than a 20% increase in the latency of the evoked response corresponding to interval $C_1$ (15 ms), interval $C_6$ is determined to be as an appropriate coupling interval for delivering the T-shock, Steps 508 and 512.

Figure 6:
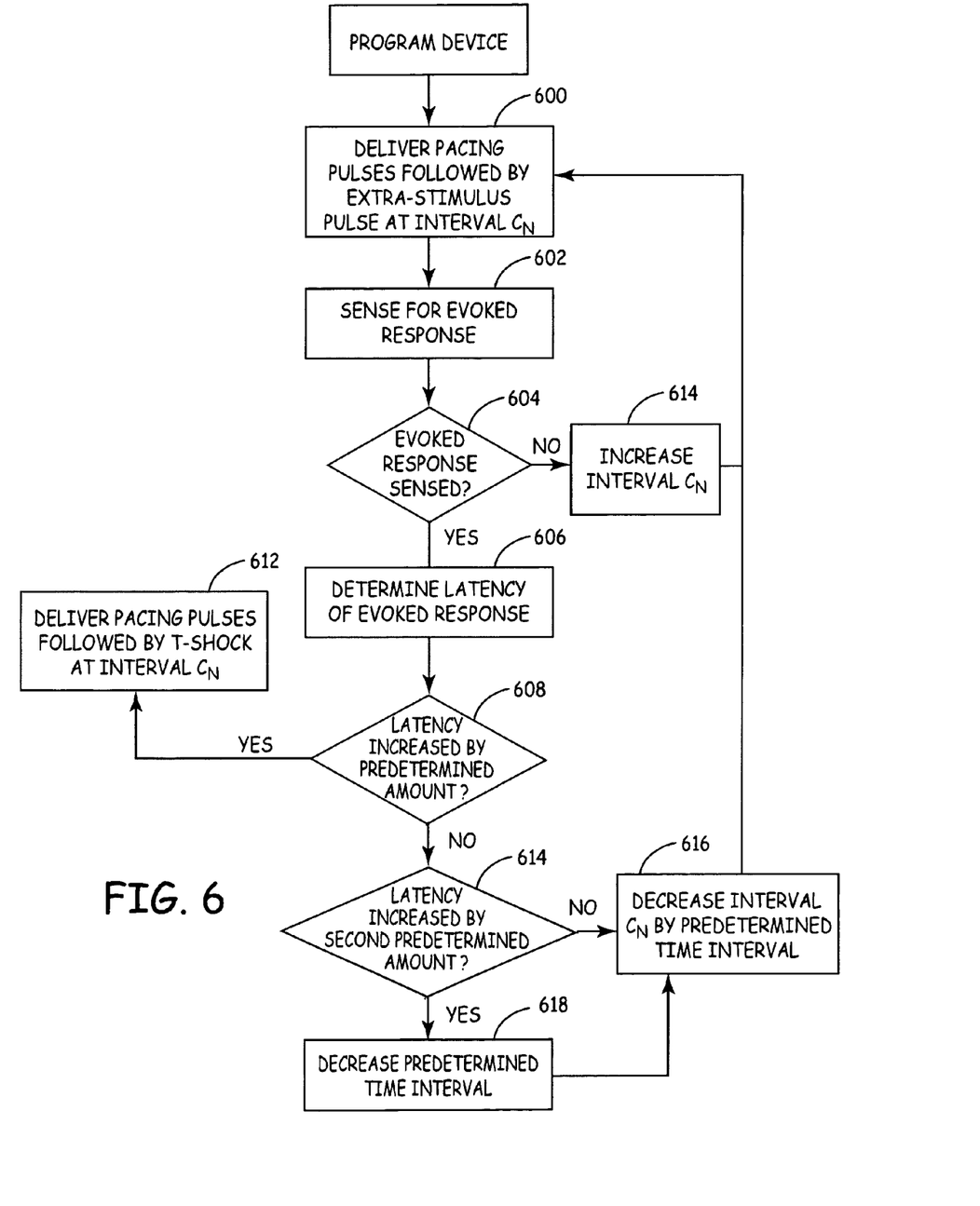
FIG. 6 is a flowchart of a method for actively determining a coupling interval according to the present invention.

FIG. 6 is a flowchart of a method for actively determining a coupling interval according to the present invention. The method for actively determining a coupling interval illustrated in FIG. 6 is similar to the method described in FIG. 5, however, in the embodiment illustrated in FIG. 6, once it is determined that the latency of the evoked response has not increased by the predetermined amount, NO in Step 608, a determination is made as to whether the latency of the evoked response has increased by a second predetermined amount, Step 614.

If the latency of the evoked response has not increased by the second predetermined amount in Step 614, the next interval $C_5$ is decreased from interval $C_4$ by the predetermined time interval, i.e., 20 ms, Step 616, and the process is repeated from Step 600 for the next interval $C_5$. However, if the latency of the evoked response has increased by the second predetermined amount, YES in Step 614, the predetermined time interval is reduced by a predetermined amount, Step 618, and the next interval $C_5$ is decreased from interval $C_4$ by the reduced predetermined time interval, and the process is repeated from Step 600 for the next interval $C_5$.

Figure 7:
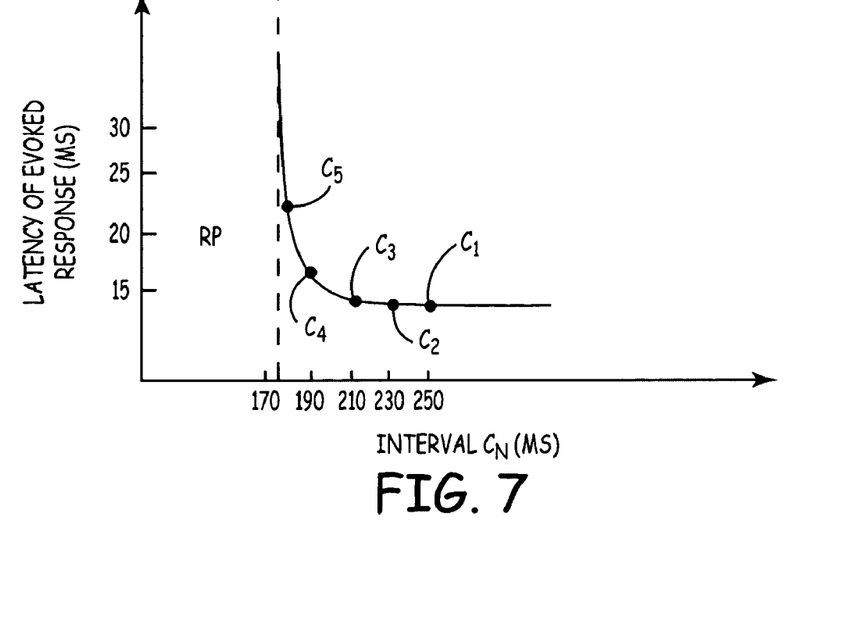
FIG. 7 is a graphical representation of an exemplary application of a method and apparatus for actively determining a coupling interval according to the present invention.

FIG. 7 is a graphical representation of an exemplary application of a method and apparatus for actively determining a coupling interval according to the present invention. According to the embodiment illustrated in FIG. 6, the second predetermined amount utilized in Step 614 is less than the predetermined amount utilized in Step 608 in order to enable the reduction in interval $C_N$ to be varied as interval $C_N$ approaches the upward trend near the refractory period. In particular, as illustrated in FIGS. 6 and 7, assuming that the predetermined amount utilized in Step 608 is a 20% increase, the second predetermined amount utilized in Step 614 is a 5% increase, and, as described above, assuming interval $C_N$ is initially set to be reduced by a predetermined time interval of 20 ms for each pacing sequence, for example, if interval $C_1$ is set as 250 ms, interval $C_2$ is set as interval $C_1$–20 ms, or 230 ms, interval $C_3$ is set as interval $C_2$–20 ms, or 210 ms, and interval $C_4$ is set as interval $C_3$–20 ms, or 190 ms. As a result, if the latency of the evoked response for interval $C_4$ is determined to be 17 ms in Step 606, the latency of the evoked response for interval $C_4$ will be determined not to have increased by the predetermined amount in Step 608 since 17 ms is less than a 20% increase from 15 ms, measured for interval $C_1$.

However, the latency of the evoked response corresponding to interval $C_4$ will be determined to have increased from the previously determined latency of the evoked response for interval $C_1$ by the second predetermined amount in Step 614, since an increase from 15 ms to 17 ms is greater than a 5% increase in the determined latency of the evoked response. The predetermined time interval is thus reduced in Step 618, with the amount of reduction being programmable. For example, according to an embodiment of the present invention the predetermined time interval is reduced from 20 ms to 10 ms, for example. The next interval $C_5$ is decreased from interval $C_4$ by the reduced predetermined time interval, i.e., interval $C_5$ is set as being equal to interval $C_4$–10 ms, or 180 ms, and the process is repeated from Step 600 for the next interval $C_5$.

Accordingly, the embodiment illustrated in FIG. 6 varies the predetermined time interval for reducing interval $C_N$ between cycles once the latency of the evoked response begins increasing by the second predetermined amount from the latency of the evoked response measured over the relatively flat range of time intervals, thus varying the incremental reduction in interval $C_N$ as interval $C_N$ approaches the refractory period RP and the vulnerability zone is identified. Gradually reducing the predetermined time interval as interval $C_N$ approaches the refractory period and the vulnerability zone is identified reduces the likelihood that the next interval $C_{N+1}$ will fall within the refractory period RF prior to identifying the interval having the required increase in the corresponding latency of the evoked response to be utilized for timing placement of the T-shock. In the example illustrated in FIG. 7, since the predetermined time interval was reduced, after it was determined that the latency of the evoked response corresponding to interval $C_4$ increased from the previously determined latency of the evoked response for interval $C_1$ by the second predetermined amount in Step 614, the next interval, interval $C_5$, was reduced from interval $C_4$ by 10 ms, rather than the initial 20 ms, preventing interval $C_5$ from falling within the refractory period.

According to an embodiment of the present invention, known morphology algorithms may be utilized to determine the location of the peak of the evoked response to obtain a more accurate measurement of the time period L between the delivery of the extra-stimulus pulse and the sensing of the evoked response when determining the latency of the evoked response in Step 506 of FIGS. 5 and 6.

Figure 8:
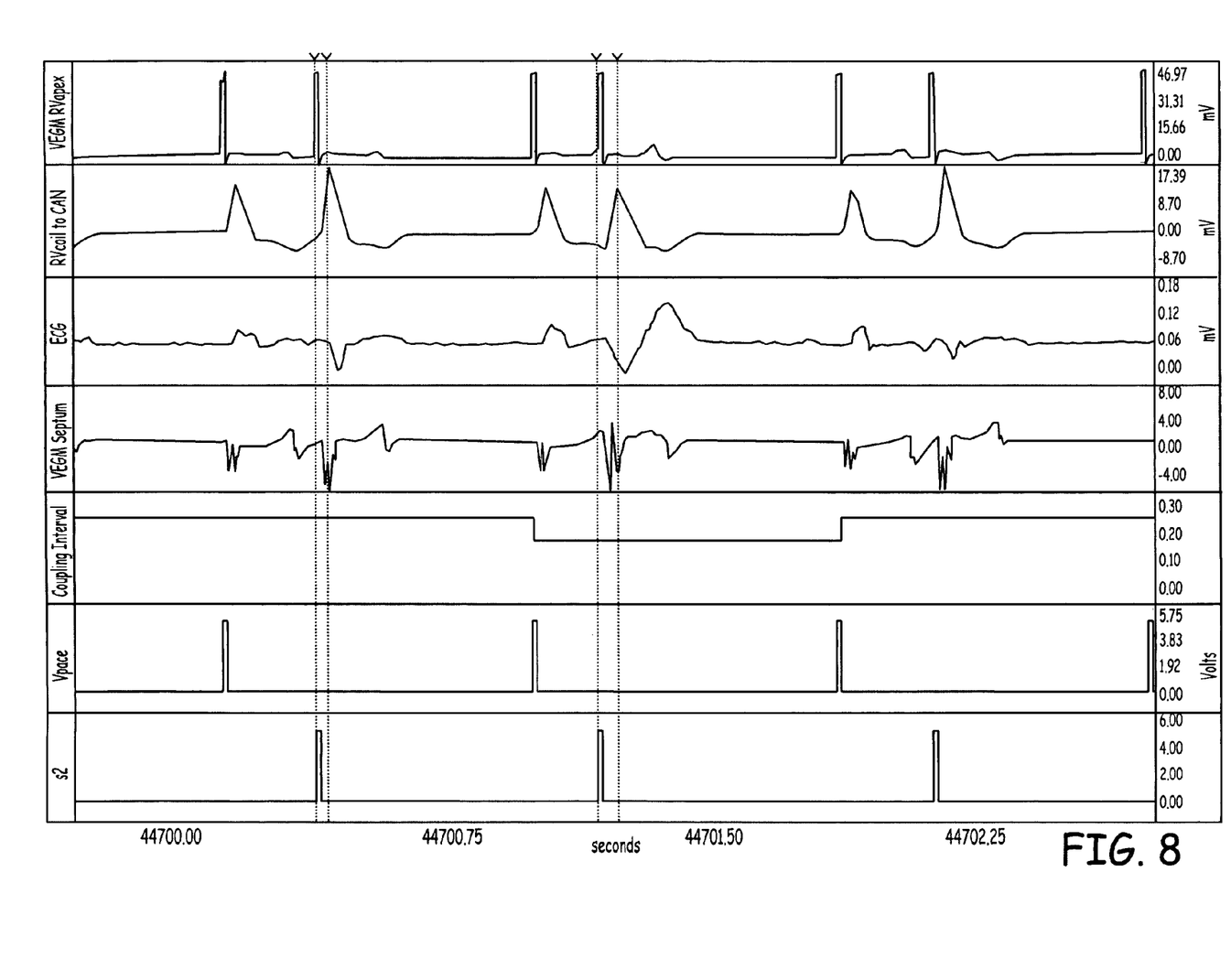
FIG. 8 is a graphical representation of an application of a method and apparatus for actively determining a coupling interval according to the present invention.

FIG. 8 is a graphical representation of an application of a method and apparatus for actively determining a coupling interval according to the present invention. According to the present invention, a dispersion of conduction and dispersion of refractoriness can be identified using means other than the latency of the evoked response, such as changes in morphology of the evoked response, for example. The morphology of the measured evoked response associated with extra-stimulus pacing pulses S2 delivered between electrodes 24 and 26, for example, at intervals outside of the vulnerability zone VZ and the refractory period RF remains relatively consistent. However, as illustrated in FIG. 8, once the placement of the extra-stimulus pacing pulse S2 approaches the refractory period RF, there tends to be a dispersion in conduction leading to changes in morphology of the evoked response, which is due to dispersion of refractoriness, indicated by the change in morphology of the evoked response. Such dispersion in refractoriness marks a likely location of the vulnerability zone VZ. Therefore, once the change in morphology of the evoked response is determined to be greater than a predetermined threshold, suggesting a dispersion of conduction and dispersion of refractoriness from the previous cycle, the interval $C_N$ associated with that change in morphology of the evoked response is then utilized for delivery of the T-shock in the next cycle. As a result, once the final pacing pulse of the subsequently generated predetermined number of pacing pulses separated by interval T1 is delivered, a T-shock is generated at the predetermined time interval $C_N$ from the delivery of final pacing pulse.

Figure 9:
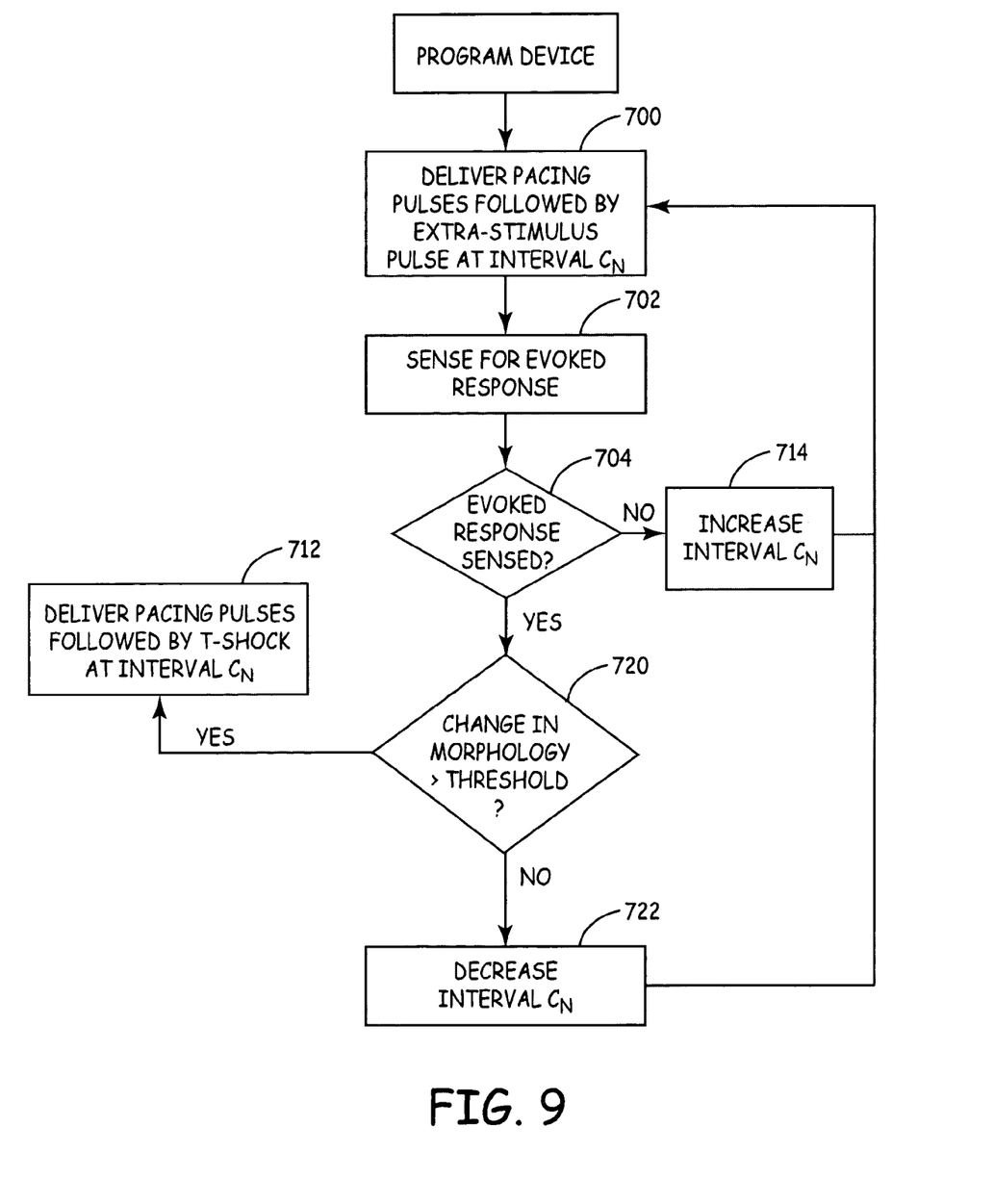
FIG. 9 is a flowchart of a method and apparatus for actively determining a coupling interval according to the present invention.

FIG. 9 is a flowchart illustrating application of a method and apparatus for actively determining a coupling interval according to the present invention. The method for actively determining a coupling interval illustrated in FIG. 9 is similar to the method described in FIG. 5, however, in the embodiment illustrated in FIG. 9, once it is determined in Step 704 that an evoked response was sensed, the morphology of the sensed evoked response is compared to a predetermined morphology template and a determination is made as to whether a change in the morphology of the sensed evoked response from the morphology template is greater than a predetermined threshold, Step 720. If the change in the morphology of the sensed evoked response is less than or equal to the predetermined threshold, NO in Step 720, time interval $C_N$ is decreased by the predetermined amount, i.e., 20 ms, Step 722, and the process is repeated using the decreased time interval $C_N$. On the other hand, if it is determined that the change in the morphology of the sensed evoked response is greater than the predetermined threshold, YES in Step 720, subsequent delivery of the predetermined number of pacing pulses separated by interval T1 is followed by delivery of a T-shock at the time interval $C_N$ associated with the increased change in morphology, Step 712. Any of the known morphology algorithms may be utilized to determine the change in morphology of the sensed evoked response without departing from the intended scope of the present invention, such as the morphology algorithm described, for example, in commonly assigned U.S. Pat. No. 6,393,316 to Gillberg et al., incorporated herein by reference in its entirety.

Figure 10:
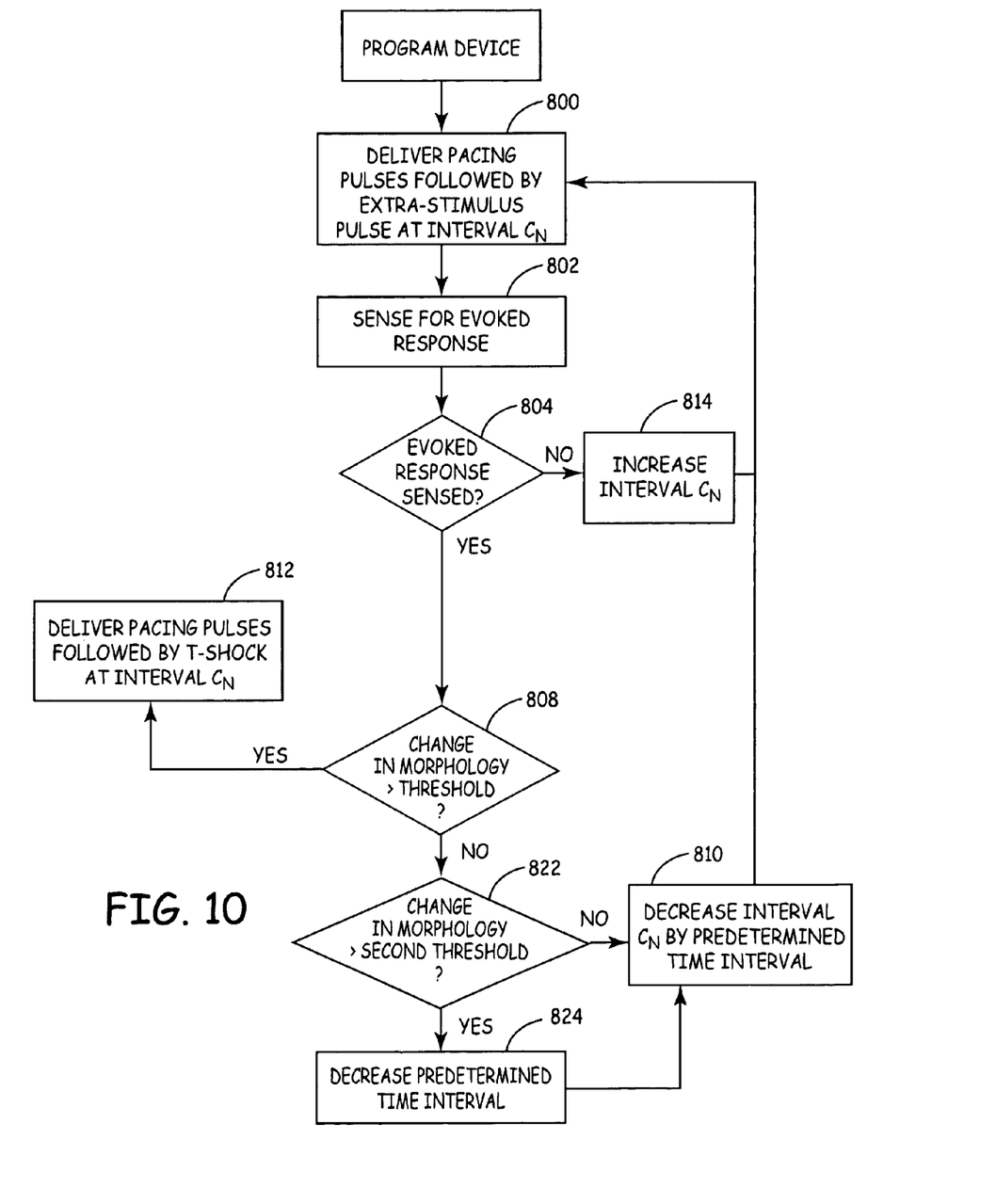
FIG. 10 is a flowchart of a method for actively determining a coupling interval according to the present invention.

FIG. 10 is a flowchart of a method for actively determining a coupling interval according to the present invention. The method for actively determining a coupling interval illustrated in FIG. 10 is similar to the method described in FIG. 8, however, in the embodiment illustrated in FIG. 10, once it is determined that the change in morphology of the sensed evoked response is not greater than the predetermined threshold, NO in Step 806, a determination is made as to whether the change in morphology of the evoked response is greater than a second predetermined threshold, Step 822. According to the embodiment illustrated in FIG. 10, the change in morphology associated with the second predetermined threshold is less than the change in morphology associated with the predetermined threshold utilized in the determination of Step 808 in order to enable the reduction in interval $C_N$ to be varied as interval $C_N$ approaches the upward trend near the refractory period.

In particular, if the change in morphology of the evoked response is not greater than the second predetermined threshold in Step 822, the next interval $C_5$ is decreased from interval $C_4$ by the predetermined time interval, i.e., 20 ms, Step 810, and the process is repeated from Step 800 for the next interval $C_5$. However, if the change in morphology of the evoked response is greater than the second predetermined threshold in Step 822, the predetermined time interval is reduced by a predetermined amount, Step 824, and the next interval $C_5$ is decreased from interval $C_4$ by the reduced predetermined time interval, Step 810, and the process is repeated from Step 800 for the next interval $C_5$.

Some of the techniques described above may be embodied as a computer-readable medium that includes instructions for a programmable processor such as microprocessor 224 or pacer timing/control circuitry 212 shown in FIG. 2. The programmable processor may include one or more individual processors, which may act independently or in concert. A "computer-readable medium" includes but is not limited to any type of computer memory such as floppy disks, conventional hard disks, CD-ROMS, Flash ROMS, nonvolatile ROMS, RAM and a magnetic or optical storage medium. The medium may include instructions for causing a processor to perform any of the features described above for actively determining a coupling interval according to the present invention.

While a particular embodiment of the present invention has been shown and described, modifications may be made. It is therefore intended in the appended claims to cover all such changes and modifications, which fall within the true spirit and scope of the invention.

The invention claimed is:

1. An apparatus comprising:
a plurality of electrodes;
a timing and control unit delivering, associated with the plurality of electrodes, a first pulse train and a first pulse signal at a predetermined time interval from delivery of a last pulse of the first pulse train;
a sensor sensing an evoked response corresponding to the first pulse signal; and
a microprocessor, coupled to the timing and control unit and the sensor, comparing the evoked response to a prior determined evoked response and determining whether a latency of the evoked response has increased by a first predetermined amount, wherein the microprocessor sets a coupling interval equal to the predetermined time interval in response to the evoked response latency having increased by the first predetermined amount, and reduces the predetermined time interval by a second predetermined amount in response to the evoked response latency not having increased by the first predetermined amount.

2. The apparatus of claim 1, wherein the microprocessor determines whether the evoked response occurs within a second predetermined time period, and increases the predetermined time interval in response to the evoked response not occurring within the second predetermined time period.

3. The apparatus of claim 1, wherein the microprocessor determines, in response to the evoked response latency not increasing by the first predetermined amount, whether the evoked response latency has increased by a third predetermined amount less than the first predetermined amount, and reduces the predetermined time interval by a fourth predetermined amount less than the second predetermined amount in response to the evoked response latency having increased by the third predetermined amount.

4. The apparatus of claim 1, wherein the microprocessor compares a morphology of the evoked response to a predetermined template, determines whether a change in the morphology of the evoked response is greater than a first predetermined threshold, and determines that the evoked response latency has increased by the first predetermined amount in response to the change in the morphology of the evoked response being greater than the first predetermined threshold.

5. The apparatus of claim 4, wherein the microprocessor determines, in response to the change in the morphology of the evoked response not being greater than the first predetermined threshold, whether the change in the morphology of the evoked response is greater than a second predetermined threshold less than the first predetermined threshold, and reduces the predetermined time interval by a third predetermined amount less than the second predetermined amount in response to the change in the morphology of the evoked response being greater than the second predetermined threshold.

6. A method of determining a coupling interval of an implantable medical device, comprising:
   delivering a first pulse train;
   delivering a first pulse signal at a predetermined time interval from delivery of a last pulse of the first pulse train;
   determining an evoked response corresponding to the first pulse signal;
   comparing the evoked response to a prior determined evoked response and determining whether a latency of the evoked response has increased by a first predetermined amount;
   setting the coupling interval equal to the predetermined time interval in response to the evoked response latency having increased by the first predetermined amount; and
   reducing the predetermined time interval by a second predetermined amount in response to the evoked response latency not having increased by the first predetermined amount.

7. The method of claim 6, further comprising:
   determining whether the evoked response occurs within a second predetermined time period; and
   increasing the predetermined time interval in response to the evoked response not occurring within the second predetermined time period.

8. The method of claim 6, further comprising:
   delivering a second pulse train;
   delivering a second pulse signal at the reduced predetermined time interval from delivery of a last pulse of the second pulse train;
   determining an evoked response corresponding to the second pulse signal;
   comparing the evoked response corresponding to the second pulse signal to the evoked response corresponding to the first pulse signal and determining whether a latency of the evoked response corresponding to the second pulse signal has increased by the first predetermined amount;
   determining whether the evoked response corresponding to the second pulse signal occurs within a second predetermined time period;
   increasing the predetermined time interval in response to the second pulse signal not occurring within the second predetermined time period;
   delivering a third pulse train; and
   delivering a third pulse signal at the increased predetermined time interval from delivery of a last pulse of the third pulse train.

9. The method of claim 8, wherein increasing the predetermined time interval in response to the second pulse signal not occurring within the second predetermined time period comprises reducing the second predetermined amount.

10. The method of claim 6, further comprising:
    determining, in response to the evoked response latency not increasing by the first predetermined amount, whether the evoked response latency has increased by a third predetermined amount less than the first predetermined amount; and
    reducing the predetermined time interval by a fourth predetermined amount less than the second predetermined amount in response to the evoked response latency having increased by the third predetermined amount.

11. The method of claim 6, wherein comparing the evoked response to a prior determined evoked response and determining whether the evoked response latency has increased by a first predetermined amount comprises:
    comparing a morphology of the evoked response to a predetermined template;
    determining whether a change in the morphology of the evoked response is greater than a first predetermined threshold; and
    determining that the evoked response latency has increased by the first predetermined amount in response to the change in the morphology of the evoked response being greater than the predetermined threshold.

12. The method of claim 11, further comprising:
    determining, in response to the change in the morphology of the evoked response not being greater than the first predetermined threshold, whether the change in the morphology of the evoked response is greater than a second predetermined threshold less than the first predetermined threshold; and
    reducing the predetermined time interval by a third predetermined amount less than the second predetermined amount in response to the change in the morphology of the evoked response being greater than the second predetermined threshold.

13. An implantable medical device, comprising:
    means for delivering a first pulse train;
    means for delivering a first pulse signal at a predetermined time interval from delivery of a last pulse of the first pulse train;
    means for determining an evoked response corresponding to the first pulse signal;
    means for comparing the evoked response to a prior determined evoked response and determining whether a latency of the evoked response has increased by a first predetermined amount;
    means for setting a coupling interval equal to the predetermined time interval in response to the evoked response latency having increased by the first predetermined amount; and
    means for reducing the predetermined time interval by a second predetermined amount in response to the evoked response latency not having increased by the first predetermined amount.

14. The device of claim 13, further comprising:
    means for determining whether the evoked response occurs within a second predetermined time period; and
    means for increasing the predetermined time interval in response to the evoked response not occurring within the second predetermined time period.

15. The device of claim 13, further comprising:
    means for delivering a second pulse train;
    means for delivering a second pulse signal at the reduced predetermined time interval from delivery of a last pulse of the second pulse train;

means for determining an evoked response corresponding to the second pulse signal;

means for comparing the evoked response corresponding to the second pulse signal to the evoked response corresponding to the first pulse signal and determining whether a latency of the evoked response corresponding to the second pulse signal has increased by the first predetermined amount;

means for determining whether the evoked response corresponding to the second pulse signal occurs within a second predetermined time period;

means for increasing the predetermined time interval in response to the second pulse signal not occurring within the second predetermined time period;

means for delivering a third pulse train; and means for delivering a third pulse signal at the increased predetermined time interval from delivery of a last pulse of the third pulse train.

16. The device of claim 15, wherein means for increasing the predetermined time interval in response to the second pulse signal not occurring within the second predetermined time period comprises means for reducing the second predetermined amount.

17. The device of claim 13, further comprising:

means for determining, in response to the evoked response latency not increasing by the first predetermined amount, whether the evoked response latency has increased by a third predetermined amount less than the first predetermined amount; and means for reducing the predetermined time interval by a fourth predetermined amount less than the second predetermined amount in response to the evoked response latency having increased by the third predetermined amount.

18. The device of claim 13, wherein means for comparing the evoked response to a prior determined evoked response and determining whether the evoked response latency has increased by a first predetermined amount comprises:

means for comparing a morphology of the evoked response to a predetermined template;

means for determining whether a change in the morphology of the evoked response is greater than a first predetermined threshold; and means for determining that the evoked response latency has increased by the first predetermined amount in response to the change in the morphology of the evoked response being greater than the predetermined threshold.

19. The device of claim 18, further comprising:

means for determining, in response to the change in the morphology of the evoked response not being greater than the first predetermined threshold, whether the change in the morphology of the evoked response is greater than a second predetermined threshold less than the first predetermined threshold; and means for reducing the predetermined time interval by a third predetermined amount less than the second predetermined amount in response to the change in the morphology of the evoked response being greater than the second predetermined threshold.

20. A computer readable medium having computer executable instructions for performing a method comprising:

delivering a first pulse train;

delivering a first pulse signal at a predetermined time interval from delivery of a last pulse of the first pulse train;

determining an evoked response corresponding to the first pulse signal;

comparing the evoked response to a prior determined evoked response and determining whether a latency of the evoked response has increased by a first predetermined amount;

setting a coupling interval equal to the predetermined time interval in response to the evoked response latency having increased by the first predetermined amount; and reducing the predetermined time interval by a second predetermined amount in response to the evoked response latency not having increased by the first predetermined amount.

* * * * *